United States Patent [19]

Naruto et al.

[11] 4,178,454

[45] Dec. 11, 1979

[54] STABILIZED PROSTAGLANDIN E COMPOSITION

[75] Inventors: Masanobu Naruto; Kiyotaka Ohno; Norio Naruse, all of Kamakura, Japan

[73] Assignee: Toray Industries, Inc., Tokyo, Japan

[21] Appl. No.: 950,451

[22] Filed: Oct. 11, 1978

[51] Int. Cl.² .................................... C07C 177/00
[52] U.S. Cl. .................................... 560/2; 562/463; 562/503
[58] Field of Search .................. 560/2; 562/503, 463

[56] References Cited

PUBLICATIONS

Glaceri et al., G. Ital. Patol. Sci. Affini 20, 41, 1974.
Chem. Abstracts 87 95617, 1977.

*Primary Examiner*—Robert Gerstl
*Attorney, Agent, or Firm*—Miller & Prestia

[57] ABSTRACT

The degradation of prostaglandins E is prevented or minimized by combining prostaglandins E with methylhesperidin.

6 Claims, No Drawings

STABILIZED PROSTAGLANDIN E COMPOSITION

This invention relates to a stabilized prostaglandin E composition.

Prostaglandins E exhibit various pharmacological activities and, when used in minor amounts, are useful in, for example, bronchodilatation, control of uterine contraction, suppression of acid secretion, treatment of and prevention against peptic ulcer, lowering of blood pressure, suppression of blood platelet aggregation and control of lipid metabolism. Prostaglandins E are generally liable to be degraded by acid, base and/or heat, and cause some problems in prescription and dosage of the medicines thereof.

When prostaglandins E are maintained at room temperature, degraded products can be detected several weeks later. At a higher temperature, for example, 100° C., a substantial part of prostaglandins E is degraded within a few hours. Even when they are maintained in a refrigerator, it is recognized that degradation proceeds, although slowly.

Some proposals have been heretofore made to stabilize prostaglandins E. For example, it is described in K. C. Srivastava and J. Clausen: Lipids, 8, p 592–594(1973) that prostaglandins E can be stabilized by dissolving them in an acid ester such as ethyl acetate, an alcohol such as ethyl alcohol, or chloroform.

It now has been found, however, that methylhesperidin prevents or minimizes the degradation of prostaglandins E to a great extent. Therefore, in accordance with the present invention there is provided a stabilized prostaglandin E composition comprising a prostaglandin E having incorporated therein a stabilizing amount of methylhesperidin.

Prostaglandins E to be stabilized by methylhesperidin include, for example, prostaglandin $E_2$ (hereinafter abbreviated as "$PGE_2$"), prostaglandin $E_1$ (hereinafter abbreviated as "$PGE_1$"), 13,14-dihydroprostaglandin $E_1$ (hereinafter abbreviated as "$PGE_0$"), 13,14-dihydro-$PGE_2$, 15-methyl-$PGE_2$, 15-methyl-$PGE_1$, 15-methyl-$PGE_0$, 16-methyl-$PGE_2$, 16-methyl-$PGE_1$, 16-methyl-$PGE_0$, 16,16-dimethyl-$PGE_2$, 16,16-dimethyl-$PGE_1$, 16,16-dimethyl-$PGE_0$, 16,16-propano-$PGE_2$, 16,16-propano-$PGE_1$, 16,16-propano-$PGE_0$, 16-cyclohexyl-$\omega$-tetranor-$PGE_2$, 16-phenyl-$\omega$-tetranor-$PGE_2$, 17-phenyl-$\omega$-trinor-$PGE_2$, 16-phenoxy-$\omega$-tetranor-$PGE_2$ and 16-m-chlorophenoxy-$\omega$-tetranor-$PGE_2$. Alkyl esters (the alkyl group having from 1 to 12 carbon atoms), such as methyl ester, ethyl ester and decyl ester, of these compounds and aralkyl esters thereof (the aralkyl group having from 7 to 15 carbon atoms) are also included in the prostaglandins E used in the present invention.

Furthermore, the prostaglandins E used in the present invention include compounds represented by the general formula:

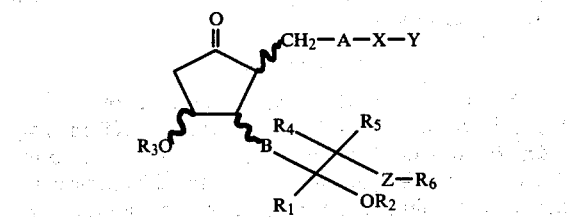

wherein:

$R_1$ represents a hydrogen atom or an alkyl group having from 1 to 4 carbon atoms;

$R_4$ and $R_5$ may be the same or different, and each of $R_4$ and $R_5$ represents independently a hydrogen atom, an alkyl group having from 1 to 4 carbon atoms or a fluorine atom;

$R_2$ and $R_3$ may be the same or different, and each of $R_2$ and $R_3$ represents independently a hydrogen atom, an alkyl group having from 1 to 4 carbon atoms or a protective group for the hydroxyl group;

$R_6$ represents an alkyl group having from 1 to 10 carbon atoms, a substituted alkyl group having from 1 to 15 carbon atoms, a cycloalkyl group having from 3 to 10 carbon atoms, a substituted cycloalkyl group (the cycloalkyl group having from 3 to 10 carbon atoms), such as 4-methyl-cyclohexyl group or 3,4-dimethyl-cyclopentyl group, an aryl group having from 6 to 15 carbon atoms, such as a phenyl group or a naphthyl group, or a substituted aryl group (the aryl group having from 6 to 15 carbon atoms), such as a phenyl or naphthyl group having from 1 to 3 substituents selected from, for example, an alkyl group having from 1 to 4 carbon atoms, a halogen atom (Cl, Br or F) and a trifluoromethyl group;

Z represents a single bond, a sulfur atom or an oxygen atom;

A represents $-CH_2CH_2-$ or cis-$-CH=CH-$;

B represents $-CH_2CH_2-$, $-C\equiv C-$ or trans-$-CH=CH-$;

X represents an alkylene group having from 1 to 5 carbon atoms or a substituted alkylene group having from 1 to 10 carbon atoms, and;

Y represents a carboxyl group, an alkoxycarbonyl group having from 2 to 13 carbon atoms, a hydroxymethyl group, an alkoxymethyl group having from 2 to 6 carbon atoms or a substituted alkoxymethyl group (the alkoxymethyl group having from 2 to 6 carbon atoms).

The prostaglandins E listed above and their preparative methods are disclosed, for example, in E. J. Corey et al: J. Am. Chem. Soc., 91, P 5675–5677(1969), ibid, 92, P 397–398(1970); Japanese Patent Publications Nos. 10,236/1973 and 24,599/1971, and; Japanese Laid-open patent applications Nos. 128,492/1976, 115,991/1976, 43,749/1976, 43,744/1976, 35,413/1976, 14,150/1976, 52,745/1973, 38,320/1972, 34,355/1972, 30,641/1972 and 6,264/1972.

The prostaglandin E's liability of being readily degraded is due to the presence of a readily eliminatable hydroxyl, acyloxy or alkoxy group in the five membered ring portion. It is usually recognized that, due to the elimination of such a readily eliminatable group, prostaglandins E are converted to prostaglandins A. The prostaglandins A are further converted to prostaglandins B and prostaglandins C, and occasionally otherwise degraded. Methylhesperidin prevents or minimizes all of such type degradations to a great extent as hereinafter explained in detail. Thus, the prostaglandins E used in the present invention should be interpreted in a broad sense as meaning all of the prostaglandins E which possess the five membered ring portion of the general formula hereinbefore mentioned.

Methylhesperidin is popularly known as a soluble vitamin P and a food additive, and is not injurious to the health. Methylhesperidin is produced by methylating hesperidin. The methylation of hesperidin is described in, for example, C. W. Wilson's U.S. Pat. No.

2,425,291(1947); I. Sakieki: Nippon Kagaku Zasshi 79, 733–736, 736–740 and 1103–1107(1958); Ibid, 80, 419–423, 423–426(1959), and; Japanese Patent Publication No. 23,091/1961 (see also Chem. Abstr., 54, 4557i and 5632f, 55, 5481e and 58, P6918d). The methylation may be effected, for example, as follows. Dimethyl sulfate is incorporated in an alkaline solution of hesperidin, and then, sulfuric acid is added thereto to adjust the pH of the reaction mixture to a value between 4 and 5. The reaction product is extracted with n-butyl alcohol and, after n-butyl alcohol is distilled off under reduced pressure, the residue is recrystallized from isopropanol thereby to obtain a yellow powder. The methylation of hesperidin may also be effected by using diazomethane or methyl iodide, instead of dimethyl sulfate, for example, as described in F. E. King and A. Robertson: J. Chem. Soc., 1931, P1704, and G. Zemplen and A. K. Tettamanti: Chem. Ber., 71, P2511(1938).

Methylhesperidin products produced by methylation of hesperidin are usually a mixture of various methylated hesperidins and hesperindin-chalcones, the composition of which mixture varies depending upon the purification degree of hesperidin used as raw material and the methylation conditions. For example, the methylhesperidin products are comprised of 3'-methylhesperidin, 3'-methyl-7-(rhamnosyl-2-methylglucosyl)hesperetin, 3,6'-dimethylhesperidin-chalcone, 3,6'-dimethyl-4'-(rhamnosyl-2-methylglucosyl)-hesperetin-chalcone and other methylated derivatives. Such methylhesperidin products, which are generally commercially available as they are, can be used without special purification in the present invention.

The manner in which methylhesperidin is incorporated in prostaglandins E is not particularly limited. For example, a prostaglandin E and methylhesperidin are mixed together in an aqueous solution form, followed by lyophilization of the aqueous solution. When a prostaglandin E used is difficult to dissolve in water, the prostaglandin E may be dissolved in a small amount of methyl alcohol or ethyl alcohol and mixed with an aqueous methylhesperidin solution, and then, the mixture may be lyophilized. Instead of the lyophilization, a mixed solution of a prostaglandin E and methylhesperidin may be evaporated into dryness under a reduced pressure. The water content in these products dried by lyophylization or evaporation should preferably be as small as possible, i.e., less than about 5% by weight.

Instead of the above-mentioned procedure ulitizing water, only a prostaglandin E may be dissolved in an organic solvent such as alcohol and ethyl acetate, and then, the solution so obtained may be mixed well with a methylhesperidin powder, followed by the removal of the organic solvent. Alternatively, a prostaglandin E and methylhesperidin may be mixed together both in a powder form by using, for example, a mortar.

The proportion of methylhesperidin to the prostaglandin E may be varied in a broad range. Usually, the ratio of methylhesperidin to the prostaglandin E is from 0.1 to 10,000 by weight, more preferably from 1 to 1,000 by weight. When the relative amount of methylhesperidin is too small, the stability of the prostaglandin E is not satisfactory. In contrast, the use of an excessive amount of methylhesperidin causes some problems in that the medical preparations become voluminous.

Various additives may be incorporated in the stabilized prostaglandin E composition of the present invention, provided that the additives do not exert a harmful influence to a salient degree on the stability of the composition. Suitable additives are those which are conventionally used as medical additives, for example, cellulose and its derivatives such as hydroxyethylcellulose, carboxymethylcellulose and methylcellulose; polysaccharides and their derivatives such as starch, dextrin, dextran and cyclodextrin; mono- and disaccharides such as sucrose, lactose, maltose, glucose, D-fructose, mannitol and sorbitol; biological substances such as protein, nucleic acid and bile acid; vitamins and their derivatives such as ascorbic acid, tocopherol and hesperidin; and inorganic substances such as bentonite and talc, food additives may be incorporated, such as antioxidants, other stabilizers, emulsifiers and sourness-imparting agents.

The composition of the present invention can be used in any medical preparation form such as injection, aerosol, suppository and peroral preparation. These medical preparations may be prepared in a conventional manner.

The stabilized prostaglandin E composition of the present invention is useful in, similarly to conventional prostaglandin E preparations, for example, bronchodilatation, control of uterine contraction, suppression of acid secretion, treatment of and prevention against peptic ulcer, lowering of blood pressure, suppression of blood platelet aggregation and control of lipid metabolism.

The following examples are included to further illustrate the present invention, but are not intended to be limiting.

In the examples, the percentage of retention of prostaglandins E was determined as follows. After a specimen of the prostaglandin E composition was left to stand at a stated temperature and for a stated period of time, water was added to the specimen to obtain an aqueous slurry. The aqueous slurry was subjected to extraction by using as an extractant an organic solvent such as ethyl acetate and chloroform. A predetermined amount of the extract solution was subjected to a thin-layer chromatography, wherein a developing solution comprised of ethyl acetate, iso-octane, acetic acid and water (the ratio by weight=110:40:20:100) was used. An aqueous diluted ammonium sulfate-sulfuric acid solution was sprayed on the developed area, followed by heating at a temperature of 180° C. for one hour to develope a color in said developed area. The density of the color-developed area was determined by using a recording densitometer (SHIMAZU CS-900). The amount of the retained prostaglandin E was calculated from a comparison of the determined density with the calibration curve of a standard prostaglandin E. The percent of retention of prostaglandin E could be expressed by the formula:

$$\% \text{ Retention} = (A/Ao) \times 100,$$

wherein A and Ao are the amount of the retained prostaglandin E and the amount of the initial prostaglandin E used, respectively.

EXAMPLE 1

Fifty mg of methylhesperidin were dissolved in 1 milli-liter of distilled water. A solution of 500 micro-g $PGE_2$ in 50 micro-liters of methanol was added to the aqueous methylhesperidin solution, and the mixture was stirred to obtain a uniform solution. The solution was lyophilized to obtain a yellow powder.

The powder was maintained at a temperature of 100° C. in an open thermostatic chamber for a predetermined period of time, and then, the % retention of prostaglandin E was determined. The results are shown in Table I, below.

In the following Examples 2 through 24 and Comparative Examples 1 through 4, the thermal degradation test of each prostaglandin E composition powder was carried out in a manner similar to that mentioned above, unless otherwise specified. The results obtained in Examples 2 through 10 and Comparative Examples 1 through 4 are shown in Table I, below.

EXAMPLE 2

The preparation procedure mentioned in Example 1 was repeated, except that the amount of methylhesperidin was changed to 20 milli-g, to obtain a yellow powder.

EXAMPLE 3

Twenty milli-g of methylhesperidine and 174 milli-g of dextrin were dissolved in 1.2 milli-liter of distilled water. A solution of 500 micro-g $PGE_2$ in 50 micro-liters of methanol was added to the aqueous methylhesperidin solution, and the mixture was stirred to obtain a uniform solution. The solution was lyophilized to obtain a light yellow powder.

EXAMPLE 4

Five hundred micro-g of $PGE_2$ were dissolved in 1 milli-liter of ethyl acetate, and then, 20 milli-g of methylhesperidin were added to the solution while it was stirred. The resultant solution was distilled under a reduced pressure to remove ethyl acetate, thereby to obtain a yellow powder.

EXAMPLE 5

The preparation procedure mentioned in Example 4 was repeated, except that ethyl alcohol was used instead of ethyl acetate thereby to obtain a yellow powder.

EXAMPLE 6

The preparation procedure mentioned in Example 1 was repeated, except that $PGE_1$ was used instead of $PGE_2$.

EXAMPLE 7

The preparation procedure mentioned in Example 1 was repeated, except that 13,14-dihydro-$PGE_1$ was used instead of $PGE_2$.

EXAMPLE 8

The preparation procedure mentioned in Example 1 was repeated, except that 16,16-dimethyl-$PGE_2$ was used instead of $PGE_2$.

EXAMPLE 9

The preparation procedure mentioned in Example 1 was repeated, except that 16,16-dimethyl-$PGE_1$ was used instead of $PGE_2$.

EXAMPLE 10

The preparation procedure mentioned in Example 1 was repeated, except that wherein 16-m-chlorophenoxy-17,18,19,20-tetranor-$PGE_2$ was used instead of $PGE_2$.

COMPARATIVE EXAMPLE 1

Five hundred micro-g of $PGE_2$ were placed in a glass ampule. The ampule was flushed with argon and then sealed.

COMPARATIVE EXAMPLE 2

Bata-cyclodextrin clathrate inclusion compound containing 500 micro-g of $PGE_2$ was combined with β-cyclodextrin to obtain 200 milli-g of a $PGE_2$ composition.

COMPARATIVE EXAMPLE 3

The $PGE_2$ composition obtained in Comparative Example 2 was placed in a glass ampule. The ampule was flushed with argon and then sealed.

COMPARATIVE EXAMPLE 4

One hundred and seventy four milli-g of dextrin were dissolved in 1.2 milli-liter of distilled water. A solution of 500 micro-g $PGE_2$ in 50 micro-liters of methanol was added to the aqueous dextrin solution, and the mixture was stirred to obtain a uniform solution. The solution was lyophilized to obtain a white powder.

Table I

| Example No. | Prostangladin | Additive (weight ratio to PGE) | Powder Preparation | % Retention of PGE(average) 100° C. 3 hours | 100° C. 7 hours | 100° C. 24 hours |
| --- | --- | --- | --- | --- | --- | --- |
| Example 1 | $PGE_2$ | methylhesperidin(×100) | lyophilization | 97 | 92 | 89 |
| 2 | $PGE_2$ | methylhesperidin(×40) | lyophilization | 97 | —88 | |
| 3 | $PGE_2$ | methylhesperidin(×40) dextrin (×348) | lyophilization | — | 84 | 80 |
| 4 | $PGE_2$ | methylhesperidin(×40) | distillation of solution in ethyl acetate | — | — | 42 |
| 5 | $PGE_2$ | methylhesperidin(×40) | distillation of solution in ethyl alcohol | — | — | 40 |
| 6 | $PGE_1$ | methylhesperidin(×100) | lyophilization | 102 | — | 88 |
| 7 | 13,14-dihydro-$PGE_1$ | methylhesperidin(×100) | lyophilization | — | — | 90 |
| 8 | 16,16-dimethyl-$PGE_2$ | methylhesperidin(×100) | lyophilization | 99 | 95 | 87 |
| 9 | 16,16-dimethyl-$PGE_1$ | methylhesperidin(×100) | lyophilization | — | 95 | 90 |
| 10 | 16-m-chlorophenoxy--17,18,19,20-tetranor-$PGE_2$ | methylhesperidin(×100) | lyophilization | — | 92 | 86 |
| Comparative Example 1 | $PGE_2$ | — | lyophilization | — | 5* | 0* |
| 2 | $PGE_2$ | β-cyclodextrin (×400) | lyophilization | — | 55 | 50 |

Table I-continued

| Example No. | Prostangladin | Additive (weight ratio to PGE) | Powder Preparation | % Retention of PGE(average) 100° C. 3 hours | 100° C. 7 hours | 100° C. 24 hours |
| --- | --- | --- | --- | --- | --- | --- |
| 3 | $PGE_2$ | β-cyclodextrin (×400) | lyophilization | — | 64* | 45* |
| 4 | $PGE_2$ | dextrin | lyophilization | — | 78 | 68 |

*Tested in argon sealed ampule

EXAMPLES 11 THROUGH 24

Methylhesperidin-$PGE_2$ compositions were prepared in a manner similar to that mentioned in Example 1, except that the proportions of methylhesperidin to $PGE_2$ were varied as shown in Table II, below. Furthermore, the thermal degradation tests were carried out at 37° C. and 50° C. for a period of 30 days. The test results are shown in Table II, below.

Table II

| Example No. | $PGE_2$ | Methylhesperiden /$PGE_2$ | Temperature (°C.) | % Retention of $PGE_2$ (average) |
| --- | --- | --- | --- | --- |
| 11 | 500γ | 2 | 50 | 18 |
| 12 | 500γ | 4 | 50 | 67 |
| 13 | 500γ | 10 | 50 | 89 |
| 14 | 500γ | 20 | 50 | 95 |
| 15 | 500γ | 40 | 50 | 97 |
| 16 | 500γ | 100 | 50 | 91 |
| 17 | 500γ | 200 | 50 | 103 |
| 18 | 500γ | 2 | 37 | 74 |
| 19 | 500γ | 4 | 37 | 97 |
| 20 | 500γ | 10 | 37 | 94 |
| 21 | 500γ | 20 | 37 | 98 |
| 22 | 500γ | 40 | 37 | 96 |
| 23 | 500γ | 100 | 37 | 96 |
| 24 | 500γ | 200 | 37 | 100 |

What we claim is:

1. A stabilized prostaglandin E composition comprising a prostaglandin E having incorporated therein a stabilizing amount of methylhesperidin.

2. A composition according to claim 1 wherein the ratio by weight of methylhesperidin to the prostaglandin E is in the range of from 0.1 to 10,000.

3. A composition according to claim 1 wherein the ratio by weight of methylhesperidin to the prostaglandin E is in the range of from 1 to 1,000.

4. A composition according to claim 1 wherein the prostaglandin E is at least one compound selected from the group consisting of prostaglandin $E_2$, prostaglandin $E_1$, 13,14-dihydroprostaglandin $E_1$, 13,14-dihydroprostaglandin $E_2$, 15-methylprostaglandin $E_2$, 15-methylprostaglandin $E_1$, 15-methyl-13,14-dihydroprostaglandin $E_1$, 16-methylprostaglandin $E_2$, 16-methylprostaglandin $E_1$, 16-methyl-13,14-dihydroprostaglandin $E_1$, 16,16-dimethylprostaglandin $E_2$, 16,16-dimethylprostaglandin $E_1$, 16,16-dimethyl-13,14-dihydroprostaglandin $E_1$, 16,16-propanoprostaglandin $E_2$, 16,16-propanoprostaglandin $E_1$, 16,16-propano-13,14-dihydroprostaglandin $E_1$, 16-cyclohexyl-ω-tetranorprostaglandin $E_2$, 16-phenyl-ω-tetranorprostaglandin $E_2$, 17-phenyl-ω-trinorprostaglandin $E_2$, 16-phenoxy-ω-tetranorprostaglandin $E_2$, 16-m-chlorophenoxy-ω-tetranorprostaglandin $E_2$, and their alkyl esters (the alkyl group having from 1 to 12 carbon atoms) and aralkyl esters (the aralkyl group having from 7 to 15 carbon atoms), and; prostaglandins E represented by the general formula:

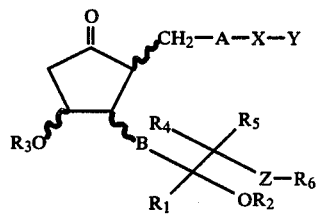

wherein $R_1$ represents a hydrogen atom or an alkyl group having from 1 to 4 carbon atoms;

$R_4$ and $R_5$ may be the same or different, and each of $R_4$ and $R_5$ represents independently a hydrogen atom, an alkyl group having from 1 to 4 carbon atoms or a fluorine atom;

$R_2$ and $R_3$ may be the same or different, and each of $R_2$ and $R_3$ represents independently a hydrogen atom, an alkyl group having from 1 to 4 carbon atoms or a protective group for the hydroxyl group;

$R_6$ represents an alkyl group having from 1 to 10 carbon atoms, a substituted alkyl group having from 1 to 15 carbon atoms, a cycloalkyl group having from 1 to 10 carbon atoms, a substituted cycloalkyl group (the cycloalkyl group having from 1 to 10 carbon atoms), an aryl group having from 6 to 15 carbon atoms, or a substituted aryl group (the aryl group having from 6 to 15 carbon atoms);

Z represents a single bond, a sulfur atom or an oxygen atom;

A represents —$CH_2CH_2$— or cis—CH=CH—;

B represents —$CH_2CH_2$—, —C≡C— or trans—CH=CH—;

X represents an alkylene group having from 1 to 5 carbon atoms or a substituted alkylene group having from 1 to 10 carbon atoms, and;

Y represents a carboxyl group, an alkoxycarbonyl group having from 2 to 13 carbon atoms, a hydroxymethyl group or an unsubstituted or substituted alkoxymethyl group (the alkoxymethyl group having from 2 to 6 carbon atoms).

5. A composition according to claim 1 wherein the methylhesperidin is a product obtained by methylating hesperidin.

6. A composition according to claim 1 which has a water content of less than about 5% by weight.

* * * * *

UNITED STATES PATENT AND TRADEMARK OFFICE
CERTIFICATE OF CORRECTION

PATENT NO. : 4,178,454
DATED : December 11, 1979
INVENTOR(S) : Masanobu Naruto et al It is certified that error appears in the above-identified patent and that said Letters Patent are hereby corrected as shown below:

Col. 3, line 21, "hesperindin-" should read --hesperidin- --.

Table I, Example 2, under the headings

| 100°C | 100°C |
|-------|-------|
| 7 hours | 24 hours |
| "   -88 | " | should read as

| -- | - 88 | --. |

Signed and Sealed this

*Twenty-fifth* Day of *March 1980*

[SEAL]

Attest:

SIDNEY A. DIAMOND

*Attesting Officer*   *Commissioner of Patents and Trademarks*